United States Patent [19]

Winter et al.

[11] 4,275,004

[45] Jun. 23, 1981

[54] HIGH CAUSTIC COUPLING PROCESS FOR PREPARING SUBSTITUTED 2-NITRO-2'-HYDROXYAZOBENZENES

[75] Inventors: Roland A. E. Winter, Armonk; Martin Dexter, Briarcliff Manor, both of N.Y.

[73] Assignee: Ciba-Geigy Corporation, Ardsley, N.Y.

[21] Appl. No.: 38,768

[22] Filed: May 16, 1979

Related U.S. Application Data

[63] Continuation-in-part of Ser. No. 918,984, Jun. 26, 1978, Pat. No. 4,226,763.

[51] Int. Cl.$^3$ .................... C07C 107/06; C09B 29/12; C07D 249/20
[52] U.S. Cl. .................... 260/206; 260/141; 260/144; 260/207; 260/45.8 NT; 548/260; 8/444; 568/718
[58] Field of Search .................... 260/205, 206, 207; 548/260

[56] References Cited

U.S. PATENT DOCUMENTS

| | | | |
|---|---|---|---|
| 2,302,955 | 11/1942 | Raiziss et al. | 260/206 X |
| 2,317,387 | 4/1943 | Kvalnes et al. | 260/206 X |
| 2,496,151 | 1/1950 | Dawson et al. | 260/206 |
| 2,538,741 | 1/1951 | Widmer et al. | 260/207 |
| 3,004,896 | 10/1961 | Heller et al. | 260/206 X |
| 3,018,269 | 1/1962 | Bruno | 548/260 X |
| 3,055,896 | 9/1962 | Boyle | 260/249.5 |
| 3,072,585 | 1/1963 | Milionis et al. | 260/22 |
| 3,074,910 | 1/1963 | Dickson | 260/45.75 |
| 3,081,314 | 3/1963 | Goel et al. | 260/206 X |
| 3,189,615 | 6/1965 | Heller et al. | 260/308 B |
| 3,208,813 | 9/1965 | Tanaka et al. | 260/206 X |
| 3,230,194 | 1/1968 | Boyle | 548/260 X |
| 3,773,751 | 11/1973 | Brooks | 260/206 |
| 4,035,423 | 7/1977 | Gallay et al. | 260/206 X |
| 4,041,044 | 8/1977 | White | 260/308 B |
| 4,127,586 | 11/1978 | Rody et al. | 260/45.8 |

FOREIGN PATENT DOCUMENTS

| | | | |
|---|---|---|---|
| 50-158588 | 12/1975 | Japan | 260/206 |
| 360357 | 11/1972 | U.S.S.R. | 260/205 |

OTHER PUBLICATIONS

Roberts et al., "Basic Principles of Organic Chemistry", pp. 892 to 895 and 897 (1965).
Fierz–David et al., "Fundamental Processes of Dye Chemistry", pp. 239 to 241 and 252 to 253 (1949).
Zollinger, "Azo and Diazo Chemistry", pp. 249 and 250 (1961).
Fierz–David et al. (II), "Fundamental Processes of Dye Chemistry", Interscience, New York, p. 251 (1949).

*Primary Examiner*—Floyd D. Higel
*Attorney, Agent, or Firm*—Luther A. R. Hall

[57] ABSTRACT

Substituted 2-nitro-2'hydroxyazobenzenes are prepared by adding an aqueous mineral acid solution of a diazotized o-nitroaniline to a strongly alkaline lower alkanol or aqueous lower alkanol solution of a substituted phenol, containing sufficient alkali metal hydroxide to assure a pH value substantially over 11 and an excess of hydroxyl ion in the reaction mixture even after all the acidic diazonium salt solution is added, wherein the reaction solvent mixture is at least 50% by weight of lower alkanol, at a reaction temperature between $-15°$ C. and $+30°$ C.

The o-nitroazobenzenes obtained are intermediate products useful in the manufacture of benzotriazole UV absorbers.

11 Claims, No Drawings

4,275,004

HIGH CAUSTIC COUPLING PROCESS FOR PREPARING SUBSTITUTED 2-NITRO-2'-HYDROXYAZOBENZENES

This is a Continuation-in-Part of application Ser. No. 918,984, filed on June 26, 1978, now U.S. Pat. No. 4,226,763, issued Oct. 7, 1980.

BACKGROUND OF THE INVENTION

The present invention relates to a process for preparing selected o-nitroazobenzene compounds which are intermediates in the subsequent preparation of 2-aryl-2H-benzotriazole UV-absorbing stabilizers.

The instant process involves the coupling of a substituted phenol with diazotized o-nitroanilines in a strongly alkaline aqueous lower alkanol solution. It is advantageous to minimize the water content in the reaction mixture in order to facilitate solubility of the substituted phenols.

The instant process is distinguished from the prior art by the use of an excess amount of alkali metal hydroxide beyond the stoichiometric amount necessary to neutralize all the mineral acid added with the acidic diazonium salt solution and to convert the phenols into their alkali salts. Accordingly throughout the instant process coupling occurs in the presence of an excess of hydroxyl ion and at a pH value substantially over 11.

The success of the instant process in preparing the instant o-nitroazobenzene intermediates is surprising in view of a panoply of existing references which teach against such a high caustic coupling process.

While the coupling of phenols with diazonium salts under moderately alkaline conditions is a well known process for the synthesis of aromatic azo derivatives, it is pointed out by J. D. Roberts and M. C. Caserio, ("Basic Principles of Organic Chemistry," W. A. Benjamin, Inc., New York (1965), pages 893–895) that the coupling procedes at a maximum rate near pH of 10 and that at higher pH values the coupling virtually ceases.

Furthermore it is known that o-nitrobenzenediazonium salt solution is unstable in the presence of alcohols and alkali metal hydroxides. Rapid decomposition takes place with the evolution of elemental nitrogen and other side reactions. For this reason the prior art teaches that excess alkali should be avoided in coupling reactions. See Fierz-David et al, "Fundamental Processes of Dye Chemistry," Interscience, New York (1949), pages 239–241, 252–253.

H. Zollinger "Azo and Diazo Chemistry," Interscience, New York (1961), pages 249–250 notes that too alkaline a solution for coupling is not recommended because the diazo equilibrium fails to remain on the side of the diazonium ions.

Russian Pat. No. 360,357 discloses the coupling of a sodium salt of a phenol in a mildly alkaline aqueous solution by the addition of an acidic diazonium salt solution having excess acid so that the pH of the reaction mixture falls rapidly during the course of the reaction to an acidic pH value well below the pH value of over 11 required for the instant process.

All of these references teach away from the instant process having an excess hydroxyl ion content and a lower alkanol cosolvent which gives high yields of the o-nitroazobenzene compounds of high purity.

DETAILED DISCLOSURE

This invention pertains to a process for preparing o-nitroazobenzene intermediates useful in the synthesis of selected 2-aryl-2H-benzotriazole light absorbers.

Specifically the instant invention provides a process for production of compounds having the formula

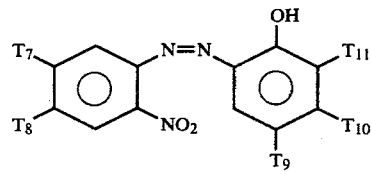

wherein
$T_7$ is hydrogen or chlorine,
$T_8$ is hydrogen, chlorine, lower alkyl of 1 to 4 carbon atoms, lower alkoxy of 1 to 4 carbon atoms, carboalkoxy of 2 to 9 carbon atoms, carboxy or $-SO_3H$,
$T_9$ is alkyl of 1 to 12 carbon atoms, alkoxy of 1 to 4 carbon atoms, phenyl, phenyl substituted with alkyl groups, said alkyl groups having 1 to 8 carbon atoms, cycloalkyl of 5 to 6 carbon atoms, carboalkoxy of 2 to 9 carbon atoms, chlorine, carboxyethyl or arylalkyl of 7 to 9 carbon atoms,
$T_{10}$ is hydrogen, lower alkyl of 1 to 4 carbon atoms, lower alkoxy of 1 to 4 carbon atoms, chlorine or hydroxyl, and
$T_{11}$ is alkyl of 1 to 12 carbon atoms, chlorine, cycloalkyl of 5 to 6 carbon atoms or arylalkyl of 7 to 9 carbon atoms,
which comprises
adding an essentially stoichiometric to a small excess amount, relevant to the phenol being coupled, of an aqueous mineral acid solution of a diazonium salt of an amine of the formula

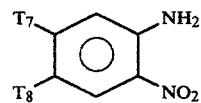

where $T_7$ and $T_8$ are defined as above, to a strongly alkaline lower alkanol or aqueous lower alkanol solution of a phenol of the formula

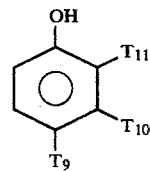

where $T_9$, $T_{10}$ and $T_{11}$ are defined as above, containing sufficient alkali metal hydroxide to assure a pH value substantially over 11 and an excess of hydroxyl ion in the reaction mixture even after all the acidic diazonium salt solution is added, while maintaining the reaction temperature between $-15°$ C. and $+30°$ C., preferably between $-2°$ C. and $+5°$ C.

After completion of the reaction, the reaction mixture is acidified conveniently with acetic acid or a mineral acid, to isolate the product, conveniently by filtration.

$T_8$ can be lower alkyl of 1 to 4 carbon atoms such as methyl, ethyl or n-butyl. $T_8$ can also be lower alkoxy of 1 to 4 carbon atoms such as methoxy, ethoxy or n-butoxy. $T_8$ can also be carboalkoxy of 2 to 9 carbon atoms such as carbomethoxy, carboethoxy, or carbo-n-octoxy.

$T_9$ can be alkyl of 1 to 12 carbon atoms such as methyl, ethyl, sec-butyl, tert-butyl, amyl, tert-octyl or n-dodecyl. $T_9$ can also be alkoxy of 1 to 4 carbon atoms such as methoxy, ethoxy or n-butoxy. $T_9$ is also phenyl substituted with alkyl groups, said alkyl groups having 1 to 8 carbon atoms such as methyl, tert-butyl, tert-amyl or tert-octyl. $T_9$ can also be cycloalkyl of 5 to 6 carbon atoms such as cyclopentyl or cyclohexyl. $T_9$ is also carboalkoxy of 2 to 9 carbon atoms such as carbomethoxy, carboethoxy, carbo-n-butoxy or carbo-n-octoxy. $T_9$ is also arylalkyl of 7 to 9 carbon atoms such as benzyl, α-methylbenzyl or α,α-dimethylbenzyl.

$T_{10}$ can be lower alkyl of 1 to 4 carbon atoms such as methyl, ethyl or n-butyl.

$T_{10}$ can also be lower alkoxy of 1 to 4 carbon atoms such as methoxy, ethoxy or n-butyloxy.

$T_{11}$ can be lower alkyl of 1 to 8 carbon atoms such as methyl, sec-butyl, tert-butyl, tert-amyl or tert-octyl.

$T_{11}$ can also be cycloalkyl of 5 to 6 carbon atoms such as cyclopentyl or cyclohexyl. $T_{11}$ is also arylalkyl of 7 to 9 carbon atoms such as benzyl, α-methylbenzyl or α,α-dimethylbenzyl.

Preferably $T_7$ is hydrogen.

Preferably $T_8$ is hydrogen, lower alkyl of 1 to 2 carbon atoms, methoxy or carboxy.

Preferably $T_9$ is alkyl of 1 to 12 carbon atoms cyclohexyl, phenyl, α-methylbenzyl, α,α-dimethylbenzyl or carboxyethyl.

Preferably $T_{10}$ is hydrogen, hydroxyl or methyl.

Preferably $T_{11}$ is alkyl of 1 to 12 carbon atoms, cyclohexyl, benzyl, α-methylbenzyl or α,α-dimethylbenzyl.

When $T_9$ and $T_{11}$ are both alkyl, the sum of their carbon atoms is preferably at least 4.

Most preferably $T_8$ is hydrogen or chlorine.

Most preferably $T_9$ is methyl, tert-butyl, tert-amyl, tert-octyl, sec-butyl, cyclohexyl, carboxyethyl, α-methylbenzyl or α,α-dimethylbenzyl.

Most preferably $T_{10}$ is hydrogen.

Most preferably $T_{11}$ is methyl, sec-butyl, tert-butyl, tert-amyl, tert-octyl, α-methylbenzyl or α,α-dimethylbenzyl.

The instant alkaline coupling process is particularly useful in the preparation of o-nitroazobenzene intermediates which cannot be made by the conventional acidic coupling process or which are prepared in the acidic coupling method only in relatively low yield. Thus the instant process is particularly valuable in preparing o-nitroazobenzenes where one or both of $T_9$ and $T_{11}$ is aralkyl such as α-methylbenzyl or α,α-dimethylbenzyl, or is tert-octyl.

The various starting materials, i.e., phenols, o-nitroaniline, 4-chloro-2-nitroaniline, α-methylstyrene, are largely available as items of commerce or can easily be prepared by known methods.

The o-nitroazobenzene intermediates are prepared by coupling the appropriate o-nitrobenzenediazonium compounds of formula

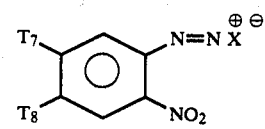

wherein $T_7$ and $T_8$ are as described previously and X is chloride, sulfate, or other anionic species, but preferably chloride, with phenols of formula

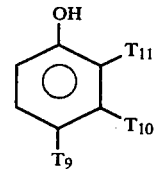

which couple in the ortho position to the hydroxy group.

The o-nitrobenzenediazonium compounds are in turn prepared by standard diazotization procedures using sodium nitrite in acid solution with the corresponding o-nitroanilines of formula

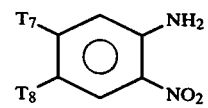

For illustration purposes some specific examples of phenols and o-nitroanilines are listed. These items are generally available as items of commerce.

Phenols 2,4-di-tert-butylphenol
2,4-di-tert-amylphenol
2,4-di-tert-octylphenol
2-tert-butyl-4-methylphenol
2,4-di(α,α-dimethylbenzyl)phenol
2,4-di-n-octylphenol
2,4-dimethylphenol
3,4-dimethylphenol
2-methyl-4-(α,α-dimethylbenzyl)phenol
2,4-dichlorophenol
3,4-dichlorophenol
2-(α,α-dimethylbenzyl)-4-methylphenol
2-(α,α-dimethylbenzyl)-4-tert-butylphonol
2-(α,α-dimethylbenzyl-4-tert-octylphenol
2-tert-octyl-4-(α,α-dimethylbenzyl)phenol
2-(α-methylbenzyl)-4-methylphenol
2-cyclohexyl-4-methylphenol
2-sec-butyl-4-tert-butylphenol
2-tert-butyl-4-sec-butylphenol
2-methyl-4-carboxyethylphenol
Preferably phenols useful in this invention are
2,4-di-tert-butylphenol
2,4-di-tert-amylphenol
2,4-di-tert-octylphenol
2-tert-butyl-4-methylphenol
2-sec-butyl-4-tert-butylphenol
2-(α-methylbenzyl)-4-methylphenol
2,4-di(α,α-dimethylbenzyl)phenol
2-(α,α-dimethylbenzyl)-4-tert-octylphenol
2-tert-octyl-4-(α,α-dimethylbenzyl)phenol o-Nitroanilines o-nitroaniline
4-chloro-2-nitroaniline
4,5-dichloro-2-nitroaniline
4-methoxy-2-nitroaniline
4-methyl-2-nitroaniline
4-ethyl-2-nitroaniline
n-butyl 3-nitro-4-aminobenzoate
n-octyl 3-nitro-4-aminobenzoate
4-n-butoxy-2-nitroaniline
3-nitro-4-aminobenzoic acid
3-nitro-4-aminobenzenesulfonic acid Preferably o-nitroanilines useful in this invention are o-nitroaniline
4-chloro-2-nitroaniline The instant process is carried out by adding an aqueous mineral acid, preferably hydrochloric acid, solution of a diazonium salt of the appropriate o-nitroaniline to a strongly alkaline aqueous lower alkanol solution of the appropriate phenol. The lower alkanol can be an alkanol of 1 to 4 carbon atoms such as methanol, ethanol, isopropanol or n-butanol, but preferably is methanol, ethanol or isopropanol and most preferably is methanol.

The instant coupling process is carried out in a manner to minimize the amount of water in the reaction mixture. Accordingly, it is preferable to use as concentrated a diazonium salt solution as can be conveniently prepared and an alkaline solution of the phenol using only the lower alkanol or an aqueous lower alkanol solution having a minimum water content. The coupling reaction is carried out in a reaction solvent mixture having at least 50% by weight of lower alkanol and preferably at least 75% by weight of lower alkanol.

The strongly alkaline alkanol or aqueous alkanol solution contains an alkali metal hydroxide such as sodium hydroxide or potassium hydroxide, preferably sodium hydroxide for reasons of economy, in sufficient amount to neutralize completely the acid diazonium salt solution as added and to still provide an excess of hydroxyl ion concentration and to provide a pH value substantially over 11 throughout the coupling reaction in the reaction mixture.

Essentially a stoichiometric amount of diazonium salt solution relative to the phenol to be coupled can be used although a small (up to 20%) excess of diazonium salt solution is conveniently used for economic considerations in the process to facilitate isolation of the product and to maximize the yield of product based on the phenol being coupled.

The benzotriazole UV absorbers made from the o-nitroazobenzene intermediates of this invention are widely used as stabilizers for organic materials especially organic polymers. The benzotriazoles have become important items of commerce.

The following examples are presented for the purpose of illustration only and are not to be construed to limit the nature or scope of the instant invention in any manner whatsoever.

EXAMPLE 1

2,4-Di-($\alpha,\alpha$-dimethylbenzyl)phenol

This intermediate was made by the general procedure of U.S. Pat. No. 2,714,120 by reacting a mixture of 705.8 grams (7.5 moles) of phenol with 1772.7 grams (15 moles) of $\alpha$-methylstyrene in the presence of 25.7 grams (0.135 moles) of p-toluenesulfonic acid monohydrate catalyst. This mixture was heated under nitrogen at 140° C. for 2.5 hours. The reaction mixture was cooled to 110° C. and 1125 ml of toluene was added. After washing the resulting solution at 80° C. with 750 ml of an aqueous solution of 37.5 grams of sodium carbonate and 75 grams of sodium chloride, the organic phase was washed thrice with 1000 ml of aqueous sodium chloride solution; then dried over anhydrous sodium sulfate; filtered and vacuum distilled. The above-named product was obtained as the main fraction boiling at 172°–175° C./0.15–0.18 mm Hg in a yield of 1229.8 grams (49.6% of theory). The product melted at 63°–65° C.

EXAMPLE 2

2-Nitro-2'-hydroxy-3',5'-di($\alpha,\alpha$-dimethylbenzyl)azobenzene Acid Coupling Process To a 2-liter, 3-necked flask fitted with a stirrer and thermometer was charged 90.6 grams of a 26% aqueous solution of technical naphthalenesulfonic acid, 1.9 grams of Triton X-207 (non-ionic surfactant), 5.6 grams of Conoco AAS-90F (sodium dodecylbenzenesulfonate) and 90 ml of water. The mixture was warmed to 40° C. and then 116.5 grams of 2,4-di($\alpha,\alpha$-dimethylbenzyl)phenol, preheated to 90° C., was slowly added to the mixture with vigorous stirring keeping the temperature at 40° C.

A cold solution of o-nitrobenzenediazonium chloride, prepared from 49.8 grams (0.36 mole) of o-nitroaniline and 24.9 grams (0.36 mole) of sodium nitrite in concentrated aqueous hydrochloric acid solution at a temperature of $-5°$ C. to 0° C., was added dropwise into the reaction mixture over a 3 hour period. The resulting deep read to black reaction mixture was kept at 40° C. overnight. The temperature was raised to 65° C. for 1 hour; then to 95° C. for another 30 minutes. After cooling to 85° C., the reaction mixture was isolated as a resinous, viscous, deep red-blank mass by filtration.

The crude product was triturated with four 200 ml portions of hot (75° C.) water; then with 400 ml of methanol overnight; and stirred in a blender with another 400 ml of methanol to yield a fine granular product. The dark red o-nitroazobenzene intermediate named above was obtained in a yield of 81.9 grams (48.4% of theory) and melted at 139°–141° C. Thin layer chromatography indicated a homogeneous product with an $R_f$ value of 0.61 on silicagel (3 cyclohexane: 1 ethyl acetate).

EXAMPLE 3

2-[2-Hydroxy-3,5-di-($\alpha,\alpha$-dimethylbenzyl)phenyl]-2H-benzotriazole

To a 5-liter 3-necked flask fitted with a stirrer, thermometer, reflux condenser and nitrogen inlet was charged 386 grams (0.805 mol) of the o-nitroazobenzene intermediate of Example 2 and 1200 ml of toluene. To the resulting solution was added 240 ml of isopropanol and 240 ml of water. A nitrogen atmosphere was imposed and 160 ml of 50.15 aqueous sodium hydroxide was added. A flask containing 158.2 grams (2.42 gram-atoms) of zinc was connected to the reaction flask by Gooch rubber tubing and the zinc dust was added portionwise to the reaction mixture over a 90-minute period. The zinc was added at such a rate to keep the internal temperature between 40° and 45° C. After the zinc was all added, the reaction mixture was heated for 1 hour at 40° C. and then for 3 hours at 70° C. The mixture was cooled to room temperature and acidified with 600 ml of concentrated hydrochloric acid.

The zinc sludge was removed by filtration. The product was contained in the organic layer, which was washed with four 340 ml portions of dilute hydrochloric acid, and was removed in vacuo to yield a crude product as a viscous syrup which crystallized on standing.

The crude product was recrystallized first from 750 ml of ethyl acetate to give 225 grams (62.5% of theory) of light tan crystals. The product was further purified by recrystallization from 1000 ml of a 4:1 mixture of acetonitrile:ethyl acetate and then dissolved in 1250 ml of toluene. The toluene solution was extracted with 70% aqueous sulfuric acid to remove colored impurities before yielding 219.3 grams (60.9% theory) of slightly off white crystals melting at 140°–141° C. of the above named compound. (Compound 1).

Analysis: Calcd for $C_{30}H_{29}N_3O$: C: 80.51; H,6.53; N:9.39. Found C: 80.53; H,6.54; N:9.51.

EXAMPLE 4

2-Nitro-2'-hydroxy-3',5'-di($\alpha,\alpha$-dimethylbenzyl)azobenzene

To a 500-ml 3-necked flask fitted with a stirrer, thermometer, pressure equalized addition funnel and nitrogen inlets and outlets were charged 13.5 grams (0.21 mole) of potassium hydroxide pellets and 10 ml of water. The resulting hot solution was diluted with 80 ml of methanol. After flushing with nitrogen, 16.5 grams (0.05 mole) of 2,4-di-($\alpha,\alpha$-dimethylbenzyl)phenol and 85 ml of methanol were added to give a clear solution which was then cooled to −4° C. A cold solution of o-nitrobenzenediazonium chloride in concentrated hydrochloric acid solution (42.9 grams = 0.06 mole of diazonium solution) was added over a period of 15 minutes with rapid stirring while keeping the temperature between −2° and 0° C. The deep purple color of the azodye-phenoxide developed instantaneously as the diazonium solution was added. The resulting mixture was stirred for another 10 minutes at −1° to 1° C. The suspension was then acidified with 20 ml of glacial acetic acid over a 2-minute period at 1° to 3° C. The resulting brick red suspension was stirred for 15 minutes as the temperature was allowed to rise to ambient temperature and then filtered. The filter cake was washed with a cold solution of 40 grams ice in 160 ml of methanol and then with 1800 ml of water.

The bright red crude product was vacuum dried at 60° C. at 75 mm Hg for 16 hours yielding 22.7 grams of material melting at 135°–140° C. Spectrometric assay indicated 86.7% purity giving a calculated yield of pure compound of 82% of theory.

The crude product was conveniently recrystallized from hot n-butanol using 5 ml per gram to give 95% recovery of pure product melting at 147°–148° C.

EXAMPLE 5

2-Nitro-2'-hydroxy-3',5'-di-($\alpha,\alpha$-dimethylbenzyl)azobenzene

Using the general procedure of Example 4, 13.6 grams (0.34 mole) of sodium hydroxide pellets were dissolved in 145 ml of methanol followed by the addition of 16.5 grams (0.05 mole) of 2,4-di-($\alpha,\alpha$-dimethylbenzyl)phenol and an additional 20 ml of methanol. The resulting solution was cooled to 2° C. Meanwhile a solution of o-nitrobenzenediazonium chloride was prepared by diazotizing a mixture of 8.3 grams (0.06 mole) of o-nitroaniline and 17.3 grams of concentrated hydrochloric acid and 6 ml of water with a solution of 4.3 grams of sodium nitrite in 8 ml of water. The diazonium solution was added gradually to the alkaline solution over a two-hour period at 2° C. The resulting deep purple reaction mixture was stirred for 30 minutes at 2° C., and then acidified with 20 ml of glacial acetic acid.

The bright red precipitate was isolated by filtration and washed successively with 3×50 ml of methanol and then with 4×75 ml of water. The product was dried at 75° C. at 75 mm Hg yielding 21.6 grams of the title compound, melting at 140°–142° C. Spectrophotometric assay indicated the product to have 97% purity giving a calculated yield of pure material of 89% of theory.

EXAMPLE 6

2-[2-Hydroxy-3,5-di-($\alpha,\alpha$-dimethylbenzyl)phenyl]-2H-benzotriazole

When in following the general procedure of Example 3 an equivalent amount of 2-nitro-2'-hydroxy-3',5'-di-($\alpha,\alpha$-dimethylbenzyl)azobenzene prepared in Example 4 was substituted for that prepared in Example 2, the above-named product was obtained in a yield of 80.2% of theory as very pale yellowish crystals melting at 139.5°–140° C. (Compound 1).

Analysis: Calcd for $C_{30}H_{29}N_3O$: C: 80.51; H,6.53; N:9.39. Found C: 80.47; H,6.28; N:9.40.

EXAMPLE 7–19

Alkaline Coupling Process

When the alkaline coupling procedure of Example 4 was used with o-nitrobenzenediazonium chloride and a variety of phenols other than 2,4-di-($\alpha,\alpha$-dimethylbenzyl)phenol, the yields of the corresponding o-nitroazobenzene products varied depending on the substitution in the phenol being coupled.

| Example | Phenols | Yield (%) of corresponding o-nitroazobenzene |
|---|---|---|
| 7 | 2,4-di-tert-amyl | 66 |
| 8 | 2,4-di-tert-octyl | 70(50)[a] |
| 9 | 2,4-di-tert-octyl | 47[b] |
| 10 | 2,4-di-($\alpha,\alpha$-dimethylbenzyl) | 82 |
| 11 | 2,4-di-($\alpha,\alpha$-dimethylbenzyl) | 89[c] |
| 12 | 2-(1-phenylethyl)-4-methyl | 84.3 |
| 13 | 4-methyl | 56[d] |
| 14 | 2,4-di-n-octyl | 56[e] |
| 15 | 2-methyl-4-$\alpha,\alpha$-dimethylbenzyl | 85* |
| 16 | 2-$\alpha,\alpha$-dimethyl benzyl-4-methyl | 66[f] |
| 17 | 2-($\alpha,\alpha$-dimethylbenzyl)-4-tert-butyl | 54 |
| 18 | 2-($\alpha,\alpha$-dimethylbenzyl)-4-tert-octyl | 62 |
| 19 | 2-tert-octyl-4-($\alpha,\alpha$-dimethylbenzyl) | 73 |
|  | control, no phenol | 0[g] |

[a]Run by procedure of Example 5 with high alkali concentration. Yield was 50% after purification. Nitrogen gas evolved = 48% theory.
[b]Nitrogen gas evolved = 60% of theory.
[c]Run by procedure of Example 5
[d]Nitrogen gas evolved = 29% of theory.
[e]Coupling in acid medium gave only a 16–19% yield of product.
[f]Nitrogen gas evolved = 33% of theory.
[g]When no phenol was present some 67% of the theoretical amount of nitrogen gas was evolved from the decomposition of the diazonium solution.
*Yield was 47% when 4-chloro-2-nitrobenzenediazonium chloride was coupled with this phenol.

EXAMPLE 20

2-Nitro-2'-hydroxy-3',5'-di(α,α-dimethylbenzyl)azobenzene

When in the procedure of Example 4 for the preparation of the above-named compound, methanol solvent was replaced with ethanol more nitrogen evolution (50% of theory) was observed with a consequently reduced yield (50.5%) of the desired o-nitroazobenzene product.

When methanol was replaced with isopropanol, again nitrogen evolution from the o-nitrobenzenediazonium chloride was 50% of theory.

These data indicate that methanol is the preferred lower alkanol solvent for the alkaline coupling process.

EXAMPLE 21

4-Chloro-2-nitro-2'-hydroxy-3',5'-di(α,α-dimethylbenzyl)azobenzene

When, using the general procedure of Example 2, an equivalent amount of the diazonium solution prepared from 4-chloro-2-nitroaniline was substituted for the diazonium solution prepared from 2-nitroaniline, the above-mentioned compound was prepared in the yield of 47.3% as a very dark red solid.

EXAMPLE 22

5-Chloro-2-[-2'-hydroxy-3',5'-di(α,α-dimethylbenzyl)-phenyl]-2H-benzotriazole

When, using the general procedure in Example 3, the amount of 4-chloro-2-nitro-2'-hydroxy-3',5'-di-(α,α-dimethyldibenzyl)azobenzene was substituted for 2-nitro-2'-hydroxy-3',5-di(α,α-dimethylbenzyl)azobenzene, the above-named compound was prepared in a yield of 70.0% as light tan crystals melting at 160°-161° C. (Compound 2)

Analysis: Calcd for C$_{30}$H$_{28}$ClN$_3$O: C: 74.45; H,5.86; N:8.72. Found C: 74.53; H,6.11; N:8.72.

EXAMPLE 23

2-Nitro-2'-hydroxy-3'-α,α-dimethylbenzyl-5'-tert-octylazobenzene

The above-named product was obtained using the general procedure of Example 5 by coupling o-nitrobenzenediazonium chloride with 2-α,α-dimethylbenzyl-4-tert-octylphenol as a red crystalline solid, melting at 133°-134° C.

EXAMPLE 24

2-(2-Hydroxy-3'-α,α-dimethylbenzyl-5'-tert-octylphenyl)-2H-benzotriazole

When in following the general procedure of Example 3, an equivalent amount of 2-nitro-2'-hydroxy-3'-α,α-dimethylbenzyl-5'-tert-octylazobenzene was substituted for the o-nitroazobenzene intermediate of Example 2, the above-named product was obtained in the form of slightly off-white crystals melting at 88°-90° C. (Compound 3)

Analysis: Calc'd for C$_{29}$H$_{35}$N$_3$O:C: 78.87; H,7.99; N,9.51. Found C: 79.21; H,8.01, N,9.55.

EXAMPLE 25

2-Nitro-2'-hydroxy-3'-tert-octyl-5'-α,α-dimethylbenzylazobenzene

When using the procedure of Example 4 o-nitrobenzenediazonium chloride was reacted with 2-tert-octyl-4-α,α-dimethylbenzylphenol, the above-named compound was obtained.

EXAMPLE 26

2-(2-Hydroxy-3-tert-octyl-5-α,α-dimethylbenzylphenyl-2H-benzotriazole

When using the procedure of Example 3, an equivalent amount of 2-nitro-2'-hydroxy-3'-tert-octyl-5'-α,α-dimethylbenzylazobenzene is substituted for the o-nitroazobenzene intermediate of Example 2, the above-named product was obtained.

What is claimed is:

1. A process for the production of a compound of the formula

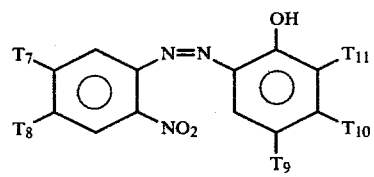

wherein
- T$_7$ is hydrogen or chlorine,
- T$_8$ is hydrogen, chlorine, lower alkyl of 1 to 4 carbon atoms, lower alkoxy of 1 to 4 carbon atoms, carboalkoxy of 2 to 9 carbon atoms, carboxy or —SO$_3$H,
- T$_9$ is alkyl of 1 to 12 carbon atoms, alkoxy of 1 to 4 carbon atoms, phenyl, phenyl substituted with alkyl groups, said alkyl groups having 1 to 8 carbon atoms, cycloalkyl of 5 to 6 carbon atoms, carboalkoxy of 2 to 9 carbon atoms, chlorine, carboxyethyl or arylalkyl of 7 to 9 carbon atoms,
- T$_{10}$ is hydrogen, lower alkyl of 1 to 4 carbon atoms, lower alkoxy of 1 to 4 carbon atoms, chlorine or hydroxy, and
- T$_{11}$ is alkyl of 1 to 12 carbon atoms, chlorine, cycloalkyl of 5 to 6 carbon atoms or arylalkyl of 7 to 9 atoms, which comprises adding an essentially stoichiometric to a small excess amount, relevant to the phenol to be coupled, of an aqueous mineral acid solution of a diazonium salt of an amine of the formula

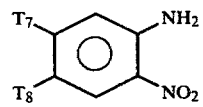

where T$_7$ and T$_8$ are defined as above, to a strongly alkaline lower alkanol or aqueous lower alkanol solution of a phenol of the formula

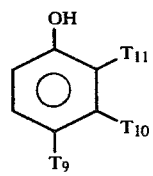

where T$_9$ T$_{10}$ and T$_{11}$ are defined as above, containing alkali metal hydroxide in sufficient amount to neutralize completely the acid diazonium salt solution as added and to still provide an excess of hydroxyl ion concentration and to provide a pH value substantially over 11 throughout the coupling reaction in the reaction mixture, wherein the reaction solvent mixture is at least 50% by weight of lower alkanol, while maintaining the reaction temperature between $-15°$ C. and $+30°$ C., and acidifying the reaction mixture to isolate the product.

2. A process according to claim 1 for the production of a compound wherein $T_7$ is hydrogen, $T_8$ is hydrogen, lower alkyl of 1 to 2 carbon atoms, methoxy or carboxy, $T_9$ is alkyl of 1 to 12 carbon atoms cyclohexyl, phenyl, α-methylbenzyl, α,α-dimethylbenzyl or carboxyethyl, $T_{10}$ is hydrogen, hydroxyl or methyl, and $T_{11}$ is alkyl of 1 to 12 carbon atoms, cyclohexyl, benzyl, α-methylbenzyl or α,α-dimethylbenzyl.

3. A process according to claim 1 for the production of a compound wherein $T_7$ is hydrogen, $T_8$ is hydrogen or chlorine, $T_9$ is methyl, sec-butyl, tert-butyl, tert-amyl, tert-octyl, cyclohexyl, carboxyethyl, α-methylbenzyl or α,α-dimethylbenzyl, $T_{10}$ is hydrogen, and $T_{11}$ is methyl, tert-butyl, sec-butyl, tert-amyl, tert-octyl, α-methylbenzyl or α,α-dimethylbenzyl.

4. A process according to claim 3 for the production of a compound wherein one or both of $T_9$ and $T_{11}$ is tert-octyl, α-methylbenzyl or α,α-dimethylbenzyl.

5. A process according to claim 1 for the production of 2-nitro-2'-hydroxy-3',5'-di(α,α-dimethylbenzyl)azobenzene.

6. A process according to claim 1 for the production of 4-chloro-2-nitro-2'-hydroxy-3',5'-di(α,α-dimethylbenzyl)azobenzene.

7. A process according to claim 1 for the production of 2-nitro-2'-hydroxy-3'-α,α-dimethylbenzyl-5'-tert-octylazobenzene.

8. A process according to claim 1 for the production of 2-nitro-2'-hydroxy-3',5'-di-tert-octylazobenzene.

9. A process according to claim 1 for the production of 2-nitro-2'-hydroxy-3'-tert-octyl-5-α,α-dimethylbenzylazobenzene.

10. A process according to claim 1 wherein the reaction temperature is maintained at $-2°$ C. to $+5°$ C.

11. A process according to claim 1 wherein the lower alkanol is methanol.

* * * * *